United States Patent [19]

Ward

[11] Patent Number: 5,177,283
[45] Date of Patent: Jan. 5, 1993

[54] HYDROCARBON CONVERSION PROCESS
[75] Inventor: Dennis J. Ward, St. James City, Fla.
[73] Assignee: UOP, Des Plaines, Ill.
[21] Appl. No.: 829,813
[22] Filed: Feb. 3, 1992
[51] Int. Cl.$^5$ .................... C07C 2/64; C07C 5/22; C07C 41/05
[52] U.S. Cl. .................... 585/446; 585/450; 585/477; 585/734; 568/697; 203/DIG. 6; 203/DIG. 9
[58] Field of Search .................... 585/446, 450, 734; 568/697, 477; 203/DIG. 6, DIG. 19

[56] References Cited

U.S. PATENT DOCUMENTS

| | | | |
|---|---|---|---|
| 2,403,672 | 7/1946 | Matuszak | 260/683.2 |
| 2,839,588 | 6/1958 | Parker | 260/635 |
| 3,215,752 | 11/1965 | Vermillion, Jr. | 260/683.48 |
| 3,506,408 | 4/1970 | Kageyama et al. | 23/288 |
| 3,579,309 | 5/1971 | Sennewald et al. | 23/288 |
| 3,634,535 | 11/1972 | Haunschild et al. | 260/677 A |
| 4,051,191 | 9/1977 | Ward | 260/671 R |
| 4,777,322 | 11/1988 | Hoelderich et al. | 585/666 |
| 4,849,569 | 7/1989 | Smith, Jr. | 585/446 |
| 5,055,627 | 10/1991 | Smith, Jr. et al. | 585/467 |

Primary Examiner—Asok Pal
Assistant Examiner—P. Achutamurthy
Attorney, Agent, or Firm—Thomas K. McBride; John F. Spears, Jr.

[57] ABSTRACT

Alkylaromatic hydrocarbons are produced in a process which comprises concentrating a feed aromatic hydrocarbon into a sidecut stream removed from a fractionation column. A feed acyclic olefin is then admixed with the aromatic hydrocarbon and passed through an alkylation reaction zone operated at optimum alkylation conditions. The reaction zone effluent is returned to the fractionation column to recover the product and to recycle untreated feed aromatics. This technique can be applied to hydrocarbon conversion processes in general to obtain benefits of catalytic distillation while operating the reaction zone at conditions not suitable for catalytic distillation. Hydrogen and other light gases are preferably separated from the reaction zone effluent by cooling and vapor-liquid separation external to the column.

18 Claims, 1 Drawing Sheet

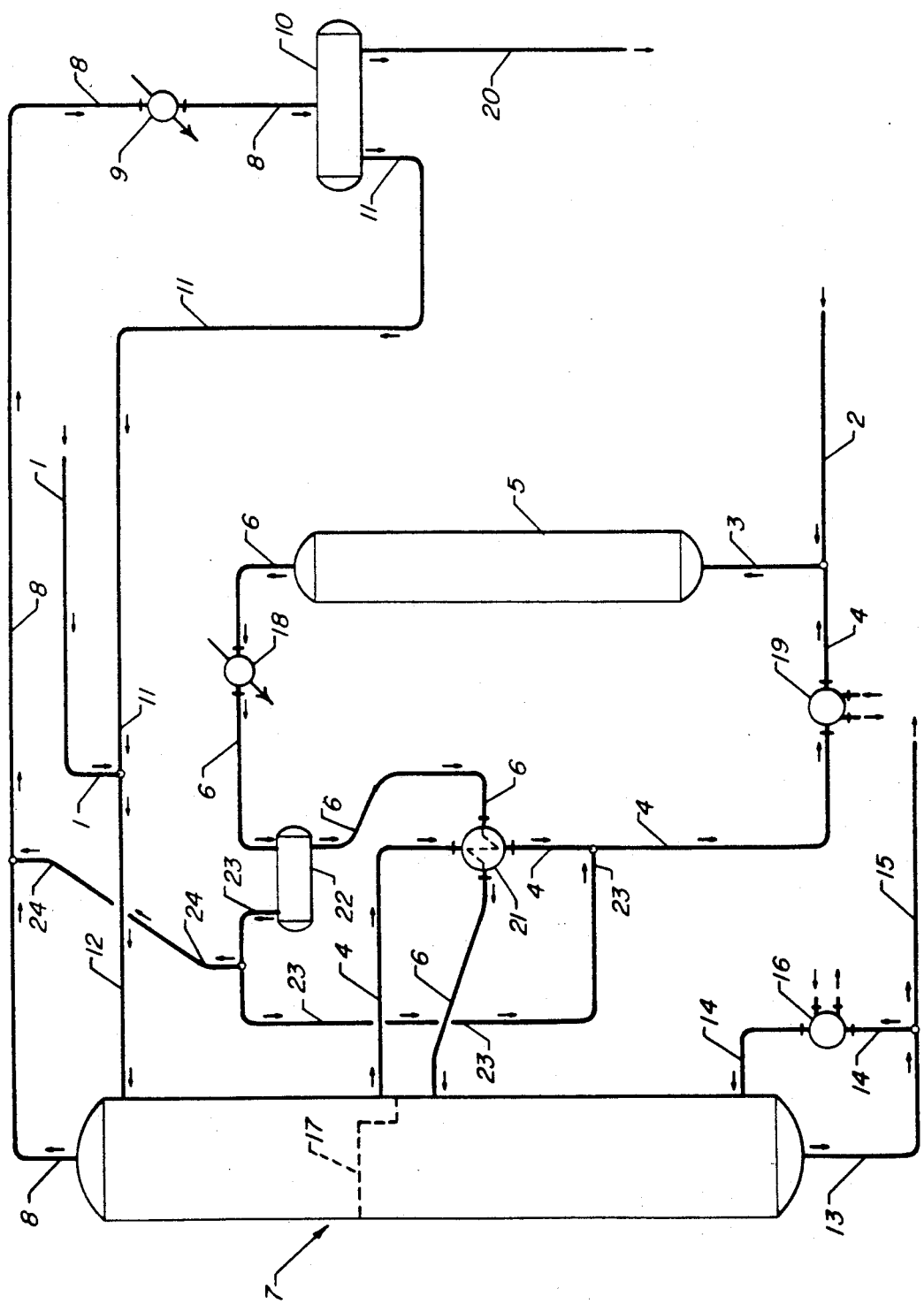

HYDROCARBON CONVERSION PROCESS

FIELD OF THE INVENTION

The invention relates to a hydrocarbon conversion process useful in the etherification, hydration and alkylation of hydrocarbons. The invention specifically relates to a process wherein an aromatic hydrocarbon is reacted with an olefinic hydrocarbon to form an alkylaromatic hydrocarbon. The subject invention is specifically directed to a process flow utilizing a fractionation column, with the feed stream to an external reaction zone being removed from the column at an intermediate point just above the point at which the liquid-phase portion of the reactor effluent is passed into the column.

PRIOR ART

The catalytic alkylation of aromatic hydrocarbons with light olefinic hydrocarbons is a widely practiced commercial process which is well described in the literature. U.S. Pat. No. 4,051,191 to D. J. Ward is believed to be pertinent for its description of traditional process flows and product recovery methods for the alkylation of aromatic hydrocarbons. This reference also is pertinent for its description of solid phosphoric acid (SPA) catalysts and their use in alkylation processes.

Catalytic distillation is now emerging as a commercially viable hydrocarbon and petrochemical processing tool. It was suggested in the past to apply catalytic distillation to a wide variety of processes such as butene isomerization (U.S. Pat. No. 2,403,672 to M. P. Matuzak) and the hydrolysis of low molecular weight olefin oxides to produce mono-alkylene glycols (U.S. Pat. No. 2,839,588 to A. S. Parker). Advantages attributed to this concept, wherein reaction products are continuously separated from the reactants and removed from the reaction zone by fractional distillation performed concurrently with the reaction, are often described as including a decrease in the capital cost of the plant needed to perform the process, the ability to achieve a higher degree of conversion, and the ability to perform processes which formerly were performed only in a batch type operation on a continuous basis. These advantages result from performing the reaction in a separation zone capable of removing the reaction products from the reactants and catalyst. Hence it is only necessary to provide one primary vessel and the reaction is not limited by chemical equilibrium. U.S. Pat. No. 3,215,752 issued to W. L. Vermillion is believed pertinent for its showing of alkylation being conducted in a rectifying column to instantaneously separate reaction products as they are formed. This reference is directed primarily to the production of motor fuel by the alkylation of light isoparaffins with olefins using the prevalent liquid phase catalysts but does refer in general terms to the processing concept.

Advances in the art of catalysis have now made it possible to apply this same processing technique to hydrocarbon alkylation using a solid catalyst. An example of this is shown in U.S. Pat. Nos. 4,849,569 and 5,055,627 issued to L. A. Smith. These references are believed to be pertinent for its showing of the use of catalytic distillation for the alkylation of aromatic hydrocarbons with a $C_2$-$C_{10}$ olefin.

U.S. Pat. No. 3,506,408 to O. Kageyama et al. illustrates the use of catalytic distillation for carrying out reversible liquid phase reactions such as the production of acetals and esters by the reaction of two organic feed compounds. This reference teaches the use of ion exchange resin particles located on shelves with layers of packing such as Raschig rings located above the catalyst.

U.S. Pat. No. 3,579,309 to K. Sennewald et al. is believed pertinent for its showing that organic chemical reactions such as the production of esters or ethers in a column which has small beds of catalyst located externally to the column.

U.S. Pat. No. 3,634,535 to W. Haunschild is pertinent for its showing that methyl tertiary butyl ether (MTBE) can be produced by catalytic distillation.

BRIEF SUMMARY OF THE INVENTION

The invention is a hydrocarbon conversion process having many of the advantages of catalytic distillation but which does not actually employ catalytic distillation. It has the advantages of allowing the use of optimum reaction conditions which are not commercially practical with catalytic distillation. In the preferred embodiment of the subject process, aromatic hydrocarbons which are fed to the reaction zone are withdrawn from a fractionation column as a sidecut stream. The temperature of this stream is adjusted as needed and it is then admixed with an olefinic feed hydrocarbon. This admixture is then passed through the reaction zone at optimum alkylation conditions for the reactants and catalyst being employed. The resultant reaction zone effluent stream is then returned to the fractionation zone near the point of withdrawal of the sidecut stream. The product of the alkylation reaction is recovered in the bottoms product stream removed from the fractionation zone. In an alternative embodiment the mixed-phase reactor effluent is separated into liquid and vapor phase portions. This allows recycling of hydrogen in the reactor effluent and avoids passing incondensible gases into the column.

BRIEF DESCRIPTION OF THE DRAWING

The drawing is a simplified process flow diagram illustrating the use of the subject invention in the alkylation of aromatic hydrocarbons. A feed stream comprising benzene is passed into the process via line 1, with the benzene traveling downward through the fractionation column 7 before flowing into the alkylation reaction zone 5. Olefins charged via line 2 react with the benzene to form alkylaromatic hydrocarbons recovered from the column in line 15. An optional vapor-liquid separator 22 allows recycling of vapor to the reactor if this is desired.

DETAILED DESCRIPTION AND PREFERRED EMBODIMENTS

Large quantities of alkylaromatic hydrocarbons are produced by various processes for the alkylation of aromatic hydrocarbons. These processes have proven highly dependable and often produce a very high quality product. However, the continuous quest for more economical alkylation processes is driving the development of alkylation processes employing "catalytic distillation". In these processes, the alkylation catalyst is retained within a structure or container capable of promoting vapor-liquid contact and fractional distillation. The overall apparatus normally resembles a fractionation column. This apparatus is provided with means to effect reflux and reboiling of the apparatus. In the case of exothermic reactions such as alkylation, the heat released by the reaction is allowed to vaporize a portion of the reactants. This causes the more volatile reactants to pass upward through the overall apparatus while the less volatile product hydrocarbons flow downward in a liquid phase. This allows a facile method for separating the product from the reactants. This fractionation within the reaction zone aids in product recovery but more importantly also tends to drive the alkylation reaction to completion by removing the product and supplying fresh reactants. A very high degree of conversion can therefore be achieved by employing catalytic distillation. The previously cited references describe the process in detail.

Catalytic distillation requires the reaction zone to be operated at conditions which allow for the presence of liquid phase compounds and also the vaporization of one or more of the reactants. These conditions may not be the optimum conditions to perform the desired reaction. For instance, it is very difficult to match the commercially desired operating temperature and pressure of the catalysts widely used for the isomerization of $C_5$–$C_6$ paraffins with the conditions required for fractional distillation. At lower pressures the conversion is reduced and the process becomes economically unattractive. Also, some reactions are best performed in vapor or liquid phase conditions rather than in the mixed-phase conditions of catalytic distillation. Other processes require the presence of hydrogen to avoid catalyst deactivation. It must also be noted that reactions occurring in the catalytic distillation zone change both the temperature and reactant concentration profiles within the catalyst containing zone of the apparatus. This may cause some sections of the catalyst-containing zone to contain an overabundance of a reactant, while other parts are starved for the reactants. It can also result in the majority of the reaction being performed in a shallow portion of the overall catalyst bed resulting in a degradation of performance. It is therefore an objective of the subject invention to provide a hydrocarbon conversion process which provides the benefits of catalytic distillation without employing catalytic distillation. It is a specific objective of the invention to provide an alkylation process which provides the benefits of catalytic distillation while allowing operation of the reaction zone with all of the reactants present in a vapor or a liquid phase. It is a further objective of the invention to simulate catalytic distillation for performing a process which requires the presence of a substantial hydrogen concentration.

The subject invention can be employed in essentially any hydrocarbon conversion process which is amendable to catalytic distillation. It can therefore be applied to light paraffin alkylation for the production of motor fuel, benzene alkylation for the production of $C_{20}$–$C_{26}$ linear alkylbenzene for use as detergent precursors, the transalkylation of $C_9$ alkylaromatics, oligomerization, esterification reactions such as the reaction of aliphatic alcohols with acetic or acrylic acids, etherification reactions for the production of methyl tertiary butyl ethers (MTBE) and tertiary amyl ethers (TAME) hydration reactions for the production of alcohols, e.g., t-butyl alcohol from butylene and halogenation reactions. Catalytic distillation principles can also be applied when there is no addition reaction such as reactions for the isomerization of $C_4$–$C_8$ paraffins, alkyl aromatics and acyclic olefins such as the double bond isomerization of butene-1 to butene-2.

The preferred embodiment of the subject process, aromatic alkylation, consumes two different reactants. The first is a light ($C_2$–$C_6$) acyclic olefin such as ethylene, propylene, a butylene or a pentene. The second reactant is a $C_6$–$C_9$ feed aromatic hydrocarbon such as benzene, toluene, a phenol or a xylene. The product hydrocarbon can therefore be one of a wide variety of $C_8$–$C_{16}$ alkylaromatic hydrocarbons including cumene and ethyltoluene. The desired product hydrocarbon may be a dialkylated aromatic but the normally intended and preferred product is a monoalkylated hydrocarbon.

The subject process can be practiced with any suitable catalyst. For alkylation this is any catalyst which gives satisfactory performance in terms of conversion and selectivity for the desired alkylation reaction. The best catalysts to employ in the subject process will of course to a great extent depend upon the identity of the specific reactants to be converted in the process. It is contemplated that aromatic alkylation can be performed using a number of acidic catalysts comprising fluorided silica alumina, dealuminated Y zeolites, or beta zeolite. It is preferred that the catalyst comprises beta zeolite if the intended reaction is the production of ethylbenzene from benzene and ethylene. The preferred catalyst for the production of cumene by the alkylation of benzene with propylene is a solid phosphoric acid (SPA) catalyst. SPA catalysts are described in U.S. Pat. Nos. 4,912,279 and 5,059,737 which are incorporated herein in their entirety for their teaching as to the production and use of SPA catalysts.

The overall flow of the invention is illustrated in the Drawing. A feed stream comprising benzene is fed into the overhead system of fractionation column 7 via line 1. This stream is preferably a high purity stream of a single feed aromatic hydrocarbon. The feed stream combines with the reflux stream carried by line 11 to form the total overhead feed stream charged to the column in line 12. The column 7 contains vapor-liquid contacting trays or packing not shown. The column is operated at conditions of temperature and pressure to effect the separation of all entering compounds into a net bottoms stream carried by line 15 and an overhead vapor stream carried by line 8. The overhead vapor stream is passed through a condenser 9, which preferably condenses the great majority of all entering hydrocarbons. The resulting liquid is collected in the overhead receiver 10. Preferably essentially all of this liquid is passed through line 11 to be returned to the column as the reflux stream. This may be specific to this embodiment in which the overhead would be expected to contain mainly benzene. If required, a portion of the overhead liquid can be removed as a net overhead stream carried by line 20. This may be desired to remove light paraffins present in the olefin feed stream of line 2. It may also be necessary to remove some vapors from the receiver 10.

The reflux fed to the top of the column causes liquid to flow downward through the column. This liquid stream is collected by means of a "trap out" tray 17 located at an intermediate point in the column and removed from the column via line 4. The benzene containing stream carried by line 4 is first passed through a feed-effluent heat exchanger 21 and is then passed through the heat exchanger 19. The stream then continues through line 4 and is admixed with a second feed stream carried by line 2 comprising propylene. The admixture of benzene and propylene, and any other hydrocarbons present in the streams of lines 2 and 4 such as propane, is passed via line 3 into the reaction zone 5 at optimum alkylation promoting conditions.

In this specific instance the materials exiting the column are near the same pressure as the reaction zone. Nevertheless, it is contemplated that a pump will be employed to pressurize this liquid phase stream and thereby enable it to flow upward through the reaction zone and return to the column. In other instances the pump may be needed to increase the pressure of the reactants to a much higher desired conversion pressure.

The reactants in this specific instance are shown as flowing upward through the fixed bed of alkylation catalyst located in the alkylation reaction zone 5 but any desired flow direction can be employed. In this specific embodiment mixed-phase conditions are preferred but in other instances such as when reacting other compounds over different catalysts vapor phase or liquid phase conditions may be preferred. The alkylation reaction itself occurs primarily in the liquid phase.

The effluent stream of the alkylation zone is carried by line 6. This stream is cooled as required in an optional cooler 18 and is then passed into an optional vapor-liquid separation zone represented by vessel 22. Uncondensed vapor is recycled to the reactor, if desired, by line 23. The liquid phase portion of the reactor effluent is then passed through the feed-effluent heat exchanger 17. The order of these two heat exchangers can be reversed. The alkylation zone effluent stream will comprise the desired alkylation product cumene, residual benzene not consumed in the reaction, by-product hydrocarbons such as dialkyl benzenes, propylene oligomers and any propane present in the propylene feed stream of line 2 and not removed in a vapor-liquid separation zone. This stream is passed into the column 7, preferably at a point just below the trap-out tray for the removal of the benzene-containing sidecut. The separation capability of the column quickly separates these hydrocarbons. The benzene and propane move upward through the column in the vapor phase while the heavier product compounds flow downward through the vapor-liquid contacting equipment (e.g. trays or structured packing) located in the bottom the column. At the bottom of the column, a bottoms stream comprising mono and dialkylated benzenes is withdrawn via line 13. A first portion is passed through line 14 and the heater 16 to reboil the column and a second portion is withdrawn in line 15 as the net bottoms stream of the column and the product stream of the process.

The separation zone 22 is not required for the alkylation embodiment of the invention. It would find more utility in those embodiments, such as olefin isomerization, in which it is desired to maintain a high concentration of hydrogen in the reaction zone. Removal of the great bulk of the hydrogen at this point would allow operating with hydrogen to feed hydrocarbon mole ratios of 0.1:1.0 to 1.0:1.0 or more. This hydrogen would be recycled to the reactor via line 23. If the olefin feed stream of line 2 contained a sizeable concentration of relatively non-reactive paraffins, it may be desired to allow the uncondensed paraffins to leave the system via line 24 to avoid overloading the column 7 with vapor. The stream of line 24 may be passed into the overhead condenser by optional line 8, if desired, to allow recovery of benzene and the product alkylate contained therein.

One embodiment of the subject invention can accordingly be characterized as a process for the alkylation of aromatic hydrocarbons which comprises the steps of passing a first feed stream comprising an aromatic feed hydrocarbon into an upper end of a fractionation zone operated under conditions which result in the separation of entering hydrocarbons into an overhead vapor stream comprising the aromatic feed hydrocarbon and any $C_6$-minus hydrocarbons which enter the fractionation zone, and a bottoms stream which comprises a product alkylaromatic hydrocarbon; withdrawing a sidecut stream from the fractionation zone at a first intermediate point separated from each functional end of the fractionation zone by contacting material capable of providing at least two theoretical stages of separation, with said sidecut stream comprising said feed aromatic hydrocarbon; passing said sidecut stream and a second feed stream comprising a $C_2$–$C_5$ olefinic hydrocarbon into a reaction zone operated at mixed-phase alkylation promoting conditions and thereby producing an alkylation zone effluent stream comprising the product alkylaromatic hydrocarbon and the feed aromatic hydrocarbon; passing the alkylation zone effluent stream into the fractionation zone at a second intermediate point and recovering a net bottoms stream comprising the alkylaromatic product hydrocarbon from the fractionation zone.

Another embodiment of the invention may be characterized as a hydrocarbon conversion process which comprises the steps of passing a feed stream comprising a feed hydrocarbon into a fractionation zone operated under conditions which result in the separation of entering hydrocarbons into an overhead vapor stream, which is rich in a product hydrocarbon, and a bottoms stream, which is rich in the feed hydrocarbon; withdrawing a sidecut stream from the fractionation zone at a first intermediate point separated from each functional end of the fractionation zone by contacting material capable of providing at least two theoretical stages of separation, with said sidecut stream comprising said feed aromatic hydrocarbon; passing said sidecut stream a hydrogen-rich gas stream into a catalytic reaction zone operated at conversion promoting conditions and thereby producing a mixed-phase reaction zone effluent stream comprising the product hydrocarbon and the feed aromatic hydrocarbon; separating the mixed-phase reaction zone into liquid and vapor-phase portions and recycling at least a fraction of said vapor portion to the reaction zone; passing the liquid-phase portion of the reaction zone effluent stream into the fractionation zone at a second intermediate point; and, recovering a net overhead product stream comprising the product hydrocarbon from the fractionation zone. As used herein, the term "rich" is intended to indicate a concentration of the indicated compound greater than 50 mole %.

The presently preferred catalyst for the alkylation of benzene with propylene is a solid phosphoric acid or SPA catalyst. A highly preferred form of this catalyst is characterized in that 25.0 percent or less of the total catalyst composite pore volume consists of pores having a diameter of 10,000 Å or larger. The solid phosphoric acid catalyst composite is further characterized in that the binder material is preferably an inorganic oxide material and most preferably a siliceous material such as diatomaceous earth, kieselguhr, or artificially prepared silicas or mixtures thereof.

In a preferred embodiment, the solid phosphoric acid catalyst composition is in the form of an extrudate and comprises phosphoric acid and an inorganic oxide binder. The preferred catalyst is characterized in that 17.5 percent or less of the catalyst composite extrudate pore volume consists of pores having diameters of 10,000 Å or larger. The catalyst is further characterized in that the total catalyst composite extrudate pore volume is about 0.28 cc/g or less with the absolute pore volume for the pores having diameters of 10,000 Å or larger being 0.07 cc/g or less. Finally, it is preferred that the instant catalyst composite comprise at least 60 wt. % $P_2O_5$.

It is preferred that the total catalyst pore volume is at most 0.28 cc/g and preferably at most 0.23 cc/g.

The essential and active ingredient of the solid phosphoric acid catalyst herein contemplated is an acid of phosphorus, preferably one in which the phosphorus has a valence of +5. The acid may constitute from about 60 to about 80 wt. % or more of the catalyst mixture ultimately produced. Of the various acids of phosphorus, orthophosphoric acid ($H_3PO_4$) and pyrophosphoric acid ($H_4P_2O_7$) find general application in the primary mixtures, due mainly to their lower cost and to the readiness with which they may be procured. The SPA catalyst composite is not restricted to their use but may employ any of the other acids of phosphorus insofar as they are adaptable. It is not intended to infer, however, that the different acids of phosphorus, which may be employed will produce catalyst which have identical affects upon any given organic reactions as each of the catalysts produced from different acids and by slightly varied procedure will exert its own characteristic action.

In using orthophosphoric acid as a primary ingredient, different concentrations of the aqueous solution may be employed from approximately 75 percent to 100 percent. An acid containing some free phosphorus pentoxide may even be used. By this is meant that the ortho acid may contain a definite percentage of the pyro acid corresponding to the primary phase of dehydration of the orthophosphoric acid. Within these concentration ranges, the acids will be liquids of varying viscosities, and will readily mix with adsorbent materials. In practice, it has been found that pyrophosphoric acid corresponding to the formula $H_4P_2O_7$ can be incorporated with binder materials at temperatures somewhat above its melting point (61° C.) and that the period of heating which is given to the pyroacid adsorbent mixtures may be different from that used when the ortho acid is so employed.

The binder material which may be employed as a component of the solid phosphoric acid catalyst composite may be any material that is able to adsorb or bind with the phosphoric acid component of the catalyst composite. One such group of material includes the refractory inorganic oxides such as alumina, silica, or other metal oxides such as oxides of magnesium, calcium, phosphorus, and titanium, or mixtures thereof to name but a few.

It is preferred that the binder material be a siliceous material. Examples of such siliceous or $SiO_2$-containing materials which are useful as the binder component of the instant solid phosphoric acid catalyst include kieselguhr, diatomaceous earth, infusorial earth, kaolin, fullers earth, or artificially prepared porous silica or mixtures thereof. It is most preferred that the siliceous binder material is kieselguhr. However, it is noted that the terms infusorial earth, kieselguhr, and diatomaceous earth and in general such naturally occurring porous siliceous materials will be used and referred to interchangeably and on an equivalent basis in general in connection with the present invention.

One method that may be used to produce a solid phosphoric acid catalyst composite having the desired pore volume characteristics of the catalyst of this invention is to closely control the particle size of the binder material. Most binder materials typically contain particles varying greatly in size. It is anticipated that by using very small sized particles of binder material, the resulting solid phosphoric acid catalyst composite will be more compact and will thus contain fewer pores greater than 10,000 Å in diameter, in comparison to a catalyst that was manufactured with larger binder particles.

In producing the catalyst composites which are utilized in the present invention, an oxygen acid of phosphorus and the solid binder material described above are mixed at a temperature of from about 10° to about 232° C. and preferably at a temperature of from about 95° to about 180° C. to form a composite. Thus, satisfactory results have been obtained by heating polyphosphoric acid (82% $P_2O_5$ content) at a temperature of about 170° C. and then mixing this hot acid with diatomaceous earth which has previously been at room temperature. The polyphosphoric acid and diatomaceous earth form a composite in which the weight ratio of phosphorus pentoxide to diatomaceous adsorbent is from about 1.5 to about 7.5. This composite is slightly moist to almost dry in appearance but becomes plastic when subjected to pressure in a hydraulic press-type or auger-type extruder by which the composite is formed into pieces that are cut into shaped particles.

The catalyst composite formed, for example by extrusion, is amorphous (or green) and must undergo a crystallization step that places the catalyst composite in a crystalline form ready for use in a hydrocarbon conversion process. Typically, the crystallization step is calcination. The calcination of the amorphous extrudate may be accomplished in any known calcination process of the prior art which controls temperature and time, and optionally, moisture level in the calcination zone. Thus, the crystallization of the catalyst may occur in a calcination apparatus containing a single calcination zone, two calcination zones, or three or more calcination zones. A calcination zone is characterized in that at least the temperature of the zone can be controlled independently of the other calcination zones.

The calcination variables noted above are believed to directly impact on the final type and amount of ores and pore volume in the calcined solid phosphoric acid catalysts. As mentioned, it is preferred that the finished solid phosphoric acid catalyst be characterized in that 25.0 percent or less of the total catalyst pore volume consists of pores having a diameter of 10,000 Å or larger. Further, it is preferred that the catalyst have a total pore volume of 0.28 cc/g or less.

The catalyst surface area and pore volume distribution are typically determined by mercury intrusion and extrusion methods. The mercury intrusion and extrusion methods are widely used in the catalysis science for catalyst porosity characterization. Detail discussion can be found in literature references such as *A Review of Mercury Porosimetry* by H. M. Rootare in Advanced Experimental Techniques in Powder Metallurgy, pp 225-252, Plenum Press, 1970.

In a continuous process for alkylating aromatic hydrocarbons with olefins, the aromatic substrate and olefinic alkylating agent are contacted at a molar ratio of from about 1:1 to 20:1 and preferably from about 2:1 to 8:1. The preferred molar feed ratios help to maximize the catalyst life cycle by minimizing the deactivation of the catalyst by coke and heavy material deposition upon the catalyst. The catalyst may be contained in one bed within a reactor vessel or divided up among a plurality of beds within a reactor. The alkylation reaction zone may contain one or more such reaction vessels in series or in parallel.

In some cases, in order to maintain the reaction temperature in the preferred range and thus reduce the formation of unwanted polyalkylaromatics, it may be desirable to quench the reactants to dissipate heat of reaction. A quench stream comprised of the alkylating agent, the feed aromatic, the alkylating agent or a portion of the reactor effluent stream, or mixtures thereof may be injected into the alkylation reactor system at various points in order to dissipate heat and supply additional amounts of olefin alkylating agent and unreacted aromatic substrate at various locations within the reaction zone. This is accomplished for example in a single-stage reactor by multiple injection of the aforementioned quench stream components into the reaction zone via strategically placed inlet lines leading into said reaction zone. The amount and composition of quench material injected into either a single stage reaction system or multi-stage reaction system may be varied according to need. Benefits resulting from multiple quench injection include elimination of costly cooling apparatus in the process, improved selectivity to formation of the desired alkylaromatic compound, provision for a larger heat sink and optimization of the olefin to aromatic compound molar ratio throughout the reaction zone, thus resulting in increased yield of the desired monoalkylated aromatic compound.

Temperatures which are suitable for use in the process herein are those temperatures which initiate a reaction between an aromatic substrate and the particular olefin used to selectively produce the desired monoalkylaromatic compound. Generally, temperatures suitable for use are from about 100° to about 390° C., especially from about 150° to about 275° C. Pressures which are suitable for use herein preferably are above about 1 atmosphere but should not be in excess of about 130 atmospheres. An especially desirable pressure range is from about 10 to about 40 atmospheres; with a liquid hourly space velocity (LHSV) based upon the benzene feed rate of from about 0.5 to about 50 $hr^{-1}$, and especially from about 1 to about 10 $hr^{-1}$. It should be noted that the temperature and pressure combination used herein is to be such that the alkylation reaction takes place in essentially the liquid phase. In a liquid phase process for producing alkylaromatics, the catalyst is continuously washed with reactants, thus preventing buildup of coke precursors on the catalyst. This results in reduced amounts of carbon forming on said catalyst in which case, catalyst cycle life is extended as compared to a gas phase alkylation process in which coke formation and catalyst deactivation is a major problem.

Additionally, a regulated amount of water is preferably added to the alkylation reaction zone. In order to substantially prevent loss of water from the catalyst and subsequent decrease in catalyst activities, an amount of water or water vapor such as steam is added to the charge so as to substantially balance the water vapor pressure of the alkylation catalyst hereinabove described. This amount of water varies from about 0.01 to 6% by volume of the organic material charged to the alkylation reaction zone. The water is then typically removed with the light by-product stream recovered in the first separation zone.

The subject process may also find great utility in the catalytic isomerization of light paraffins. The catalyst used in this process may be one of the known catalysts such as those described in U.S. Pat. Nos. 4,716,137; 2,999,074; 4,489,216 and 4,665,273 which are incorporated herein for their teaching of catalyst compositions and suitable operating conditions. A catalyst comprising mordenite and platinum is suitable. Preferred conditions include a pressure above 130 psia, e.g., from 150–1000 psig and a temperature of from about 250°–550° F. It is highly preferred to be able to operate with a minimum hydrogen partial pressure to avoid passing large amounts of hydrogen into the fractionation column.

The subject invention can also be applied to the isomerization of butylenes. This process is described for instance in U.S. Pat. No. 4,482,775 which employs a cation exchange resin as the catalyst. U.S. Pat. No. 4,849,576 teaches the isomerization of butenes over a catalyst containing about 0.001 to about 1.0 wt. % palladium on an alumina support of specified physical characteristics at a temperature of 185°–190° F. and a pressure of 400 psig. A preferred catalyst is described in U.S. patent application Ser. No. 07/670,139 which describes the composition and use of a catalyst comprising a silica alumino phosphate (SAPO). Operating conditions for butene skeletal isomerization include a pressure of 125–250 psig, a liquid hourly space velocity of 15–30 $hr^{-1}$, a temperature of 900–1100° F. and a hydrogen to hydrocarbon mole ratio greater than 1.0.

For instances such as this (butylene isomerization) where there is a desire for relatively large quantities of hydrogen, it is efficient to add a phase separator 22 in the line carrying the effluent of the reactor, which separator would be generally placed between cooler 18 and exchanger 21 allowing for the separation of the hydrogen rich vapor phase from the majority of the liquid hydrocarbon phase. This hydrogen rich vapor can then be recycled back to inlet of the reactor via lines 23 and 4 employing a small compressor, thus avoiding the complicating feature of having a noncondensible vapor in the fractionation section of the system.

Another application of this invention, outside the alkylation of aromatics is in the etherification of amylenes. In this example, a mixture comprising isopentane, 2 methyl butene 1, 2 methyl butene 2 and 2 methyl butene 3 is fed along with methanol and a small amount of hydrogen (less than 0.1 mol per mol of hydrocarbon charge) to reactor 5 via line 4. The reactor vessel contains not only a sulfonated poly divinyl benzene (such as Amberlist 300) but also as physical mixture or in adjacent sequential zones, another catalyst such as nickel on alumina that has been reduced and partially sulfided as taught in U.S. Pat. No. 3,821,123 for isomerizing the double bond of the olefin. The conditions in the reactor include a pressure required to produce a generally liquid phase, normally between 3 and 30 atmospheres with a preferred range of 4 to 10 atmospheres; temperatures in the range of 30° to 140° C. with a preferred range of 60° to 80° C.; an acid catalyst space velocity of from 0.5 to 10 with a preferred range of 1.0 to 3.0, and a double bond isomerization catalyst space velocity of from 2 to 50 with a preferred range of from 5 to 10; the methanol to isoamylene ratio can be from 1.0 to 10 with a preferred range of 1.0 to 2.0 and the hydrogen to olefin hydrocarbon ratio is from 0.001 to 0.1 with a preferred range of 0.005 to 0.04. Under these conditions, it is surprisingly found that not only do the 2 methyl butene 1 and 2 methyl butene 2 react, but also the majority of the 2 methyl butene 3 is converted to tertiary amyl ether (TAME) via intermediate conversion of the 2 methyl butene 3 to mixtures of 2 methyl butene 1 and 2 methyl butene 2, both of which are reactive with methanol over acid type catalysts. The pressure on the effluent of this reactor is reduced and the material is passed to a separator as mentioned above where the vapors, rich in hydrogen are compressed and reintroduced into the reactor via line 4 and the hydrocarbon liquid is passed via line 6 to the lower section of the fractionator.

Olefin double bond isomerization of olefinic hydrocarbons may be performed using the sulfided nickel on alumina catalyst of U.S. Pat. No. 3,821,123 which is incorporated herein for its teaching on this process. The process is operated at a temperature of 25° to 200° C., a pressure of atmospheric to 30 atmospheres, a liquid hourly space velocity of about 1 to 10 and a hydrogen concentration above 0.1 mole per mole of feed olefin.

The subject process is believed to be amendable to usage in the production of a wide range of organic chemical compounds. It is contemplated that the process could be used in the etherification of isobutylene or isoamylene with methanol. This process is used commercially for the production of these ethers for inclusion in motor fuel. The typical catalyst is an acid form sulfonic resin such as a copolymer of sulfonyl fluorovinyl ether and fluorocarbons as described in U.S. Pat. Nos. 3,784,399 and 3,849,243 or the sulfonated polystyrene resins crosslinked with divinylbenzene as described in U.S. Pat. No. 2,922,822, Various process techniques, etherification reaction conditions and product recovery methods are described in U.S. Pat. Nos. 4,219,678 to Obenous et al. and 4,282,389 to Droste et al. which are incorporated herein for this teaching.

Another contemplated reaction is the oligomerization of light olefins such as the process for oligomerization of isobutylene described in U.S. Pat. No. 4,268,700 to Vu et al. This process employs a 90%/10% silica alumina catalyst at 5°-150° C. and a pressure sufficient to maintain liquid phase conditions.

As previously mentioned the subject process can be employed for the production of alcohols by the hydration of olefins. Isopropyl alcohol and secondary butyl alcohol can be produced by the direct hydration of the corresponding $C_3$ or $C_4$ olefin performed using a sulfonic acid type resin at a temperature of about 100° to 200° C. and a pressure between 40 and 120 bar. The mole ratio of olefin to water may range from 0.5:1 to 30:1. Further information may be obtained by reference to U.S. Pat. No. 4,579,984 to Neier et al. which is incorporated herein by reference for its teaching in regard to this process. Tert-butyl alcohol can likewise be produced by the hydration of isobutylene as described in U.S. Pat. Nos. 4,307,257 and 4,360,406 using a strongly acidic cation exchange resin. The reaction would be performed using a single reactor instead of the staged reactor of the first cited reference.

What is claimed:

1. A process for the production of a product chemical compound by the reaction of a more volatile first and second feed chemical compound which comprises the steps:

(a) passing a first feed stream comprising the first feed compound into a fractionation zone operated under conditions which result in the separation of compounds present in the fractionation zone into an overhead vapor stream comprising the first feed compound, and a bottoms stream which comprises the product chemical compound;

(b) withdrawing a sidecut stream from the fractionation zone at a first intermediate point separated from each functional end of the fractionation zone by contacting material capable of providing at least two theoretical stages of separation, with said sidecut stream comprising said first feed compound;

(c) passing said sidecut stream and a second feed stream comprising the second feed compound into a catalytic reaction zone operated at conditions which promote the reaction of the first and second feed compounds to form the product compound and thereby producing a reaction zone effluent stream comprising the product compound and the first feed compound;

(d) passing the reaction zone effluent stream into the fractionation zone at a second intermediate point; and, (e) recovering a net bottoms stream comprising the product compound from the fractionation zone.

2. The process of claim 1 further characterized in that the reaction performed in the reaction zone is the hydration of an olefinic hydrocarbon.

3. The process of claim 1 further characterized in that the reaction performed in the reaction zone is the alkylation of a hydrocarbon.

4. The process of claim 3 further characterized in that the second feed compound is an acyclic olefin.

5. The process of claim 4 further characterized in that the first feed compound is an aromatic hydrocarbon.

6. The process of claim 1 further characterized in that the first feed compound is an olefinic hydrocarbon, the second feed compound is an alcohol and the product compound is an ether.

7. A hydrocarbon conversion process which comprises the steps:

(a) passing a first feed stream comprising a feed hydrocarbon into a fractionation zone operated under conditions which result in the separation of entering hydrocarbons into an overhead vapor stream, which is rich in the feed hydrocarbon, and a bottoms stream which is rich in a product compound;

(b) withdrawing a sidecut stream from the fractionation zone at a first intermediate point separated from each functional end of the fractionation zone by contacting material capable of providing at least two theoretical stages of separation, with said sidecut stream comprising said feed hydrocarbon;

(c) passing said sidecut stream and a hydrogen-rich gas stream into a catalytic reaction zone operated at conversion promoting conditions and thereby producing a mixed-phase reaction zone effluent stream comprising the product hydrocarbon and the feed aromatic hydrocarbon;

(d) separating the mixed-phase reaction zone effluent stream into liquid and vapor-phase portions and recycling at least a fraction of said vapor-phase portion to the reaction zone;

(e) passing the liquid-phase portion of the reaction zone effluent stream into the fractionation zone at a second intermediate point; and, (e) recovering a net bottoms product stream comprising the product hydrocarbon from the fractionation zone.

8. The process of claim 7 further characterized in that the feed hydrocarbon is a $C_3$-$C_6$ paraffin and the reaction comprises a bed of isomerization catalyst maintained at isomerization conditions.

9. The process of claim 7 further characterized in that the feed hydrocarbon is a $C_8$-$C_{10}$ alkylaromatic hydrocarbon and the reaction comprises a bed of isomerization catalyst maintained at isomerization conditions.

10. The process of claim 7 further characterized in that the feed hydrocarbon is a $C_4$-$C_8$ olefinic hydrocarbon.

11. A process for the alkylation of aromatic hydrocarbons which comprises the steps:
(a) passing a first feed stream comprising an aromatic feed hydrocarbon into an upper end of a fractionation zone operated under conditions which result in the separation of entering hydrocarbons into an overhead vapor stream comprising the aromatic feed hydrocarbon and any $C_6$-minus hydrocarbons which enter the fractionation zone, and a bottoms stream which comprises a product alkylaromatic hydrocarbon;
(b) withdrawing a sidecut stream from the fractionation zone at a first intermediate point separated from each functional end of the fractionation zone by contacting material capable of providing at least two theoretical stages of separation, with said sidecut stream comprising said feed aromatic hydrocarbon;
(c) passing said sidecut stream and a second feed stream comprising a $C_2$-$C_5$ olefinic hydrocarbon into a catalytic reaction zone operated at alkylation promoting conditions and thereby producing an alkylation zone effluent stream comprising the product alkylaromatic hydrocarbon and the feed aromatic hydrocarbon;
(d) passing the alkylation zone effluent stream into the fractionation zone at a second intermediate point located below said first intermediate point; and,
(e) recovering a net bottoms stream comprising the alkylaromatic product hydrocarbon from the fractionation zone.

12. The process of claim 11 further characterized in that the feed aromatic hydrocarbon is toluene.

13. The process of claim 11 further characterized in that the feed aromatic hydrocarbon is benzene.

14. The process of claim 11 further characterized in that at least a portion of the first feed stream is passed into the fractionation zone as part of the reflux liquid passed into the column.

15. The process of claim 11 further characterized in that the alkylation promoting conditions result in liquid phase reactants.

16. The process of claim 11 further characterized in that the alkylation promoting conditions result in mixed-phase reactants.

17. The process of claim 6 further characterized in that the catalytic reaction zone comprises both olefin isomerization and etherification catalysts.

18. The process of claim 10 further characterized in that the catalytic reaction zone comprises both isomerization and etherification catalysts and in that a second feed stream comprising an alcohol is passed into the catalytic reaction zone.

* * * * *